US006527740B1

United States Patent
Jackson et al.

(10) Patent No.: US 6,527,740 B1
(45) Date of Patent: Mar. 4, 2003

(54) MEDICAL REGROOMING AND DRUG DELIVERY DEVICE

(75) Inventors: Gregg A. Jackson, Mountain View, CA (US); Jenny E. Tsien, San Jose, CA (US); Vidya J. Nayak, Cupertino, CA (US); Andree L. Barker, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/470,877

(22) Filed: Dec. 22, 1999

(51) Int. Cl.[7] .............................................. A61M 31/00
(52) U.S. Cl. ................................................. 604/103.05
(58) Field of Search ..................... 604/103.05, 103.14, 604/163, 164.09, 164.13, 264

(56) References Cited

U.S. PATENT DOCUMENTS

| 3,345,988 A | 10/1967 | Vitello |
| 3,556,294 A | 1/1971 | Walack, III et al. |
| 3,967,728 A | 7/1976 | Gordon et al. |
| 5,137,512 A | * 8/1992 | Burns et al. ................. 604/163 |
| 5,217,484 A | * 6/1993 | Marks ......................... 604/907 |
| 5,334,166 A | 8/1994 | Palestrant |
| 5,409,463 A | 4/1995 | Thomas et al. |
| 5,460,616 A | 10/1995 | Weinstein et al. |

* cited by examiner

Primary Examiner—Anhtuan T. Nguyen
(74) Attorney, Agent, or Firm—Fulwider Patton Lee & Utecht, LLP

(57) ABSTRACT

A regrooming device for a balloon catheter, comprising a tubular member having a proximal section, a distal section, and an inner lumen extending therein configured to receive a balloon of a balloon catheter; and a mandrel disposed within the inner lumen and having a proximal end configured to enter a guide wire lumen at a distal section of the balloon catheter to facilitate guiding the distal section of the catheter into the inner lumen of the regrooming device, and a distal end secured to the distal section of the tubular member.

20 Claims, 4 Drawing Sheets

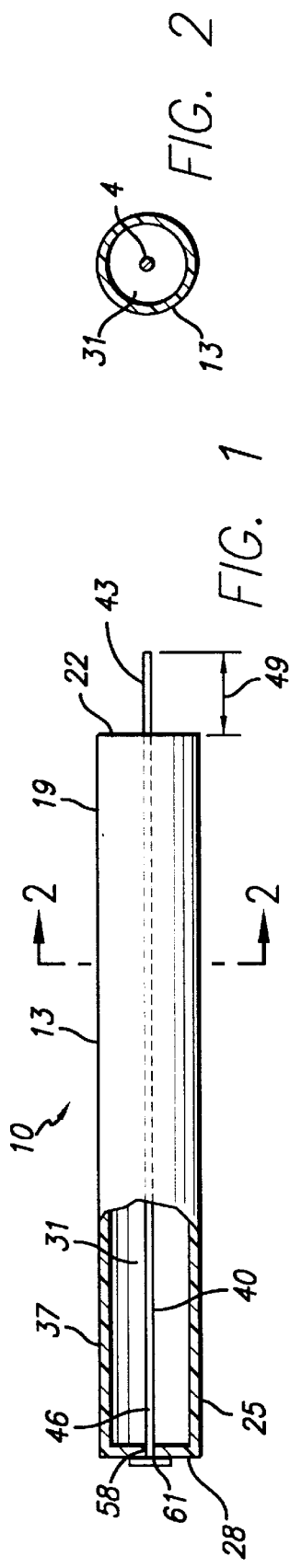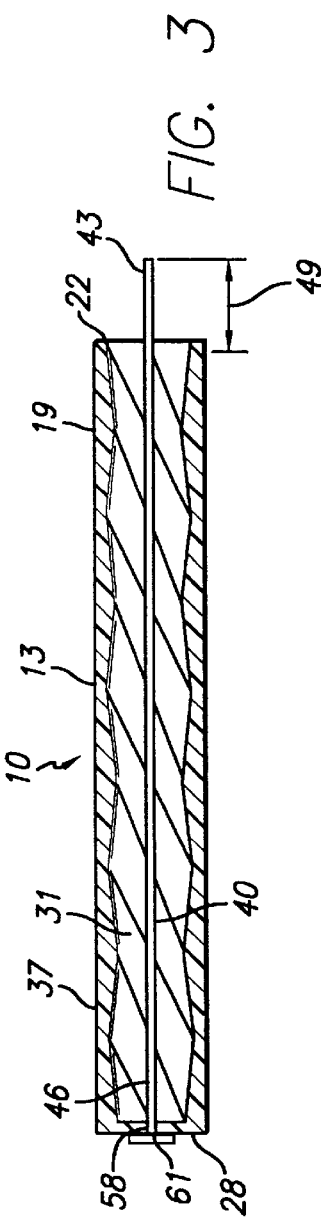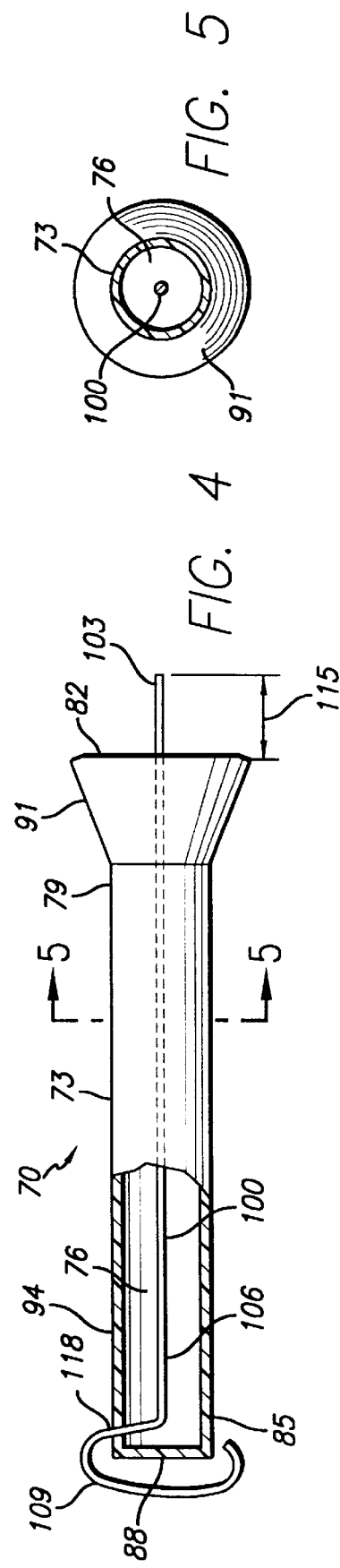

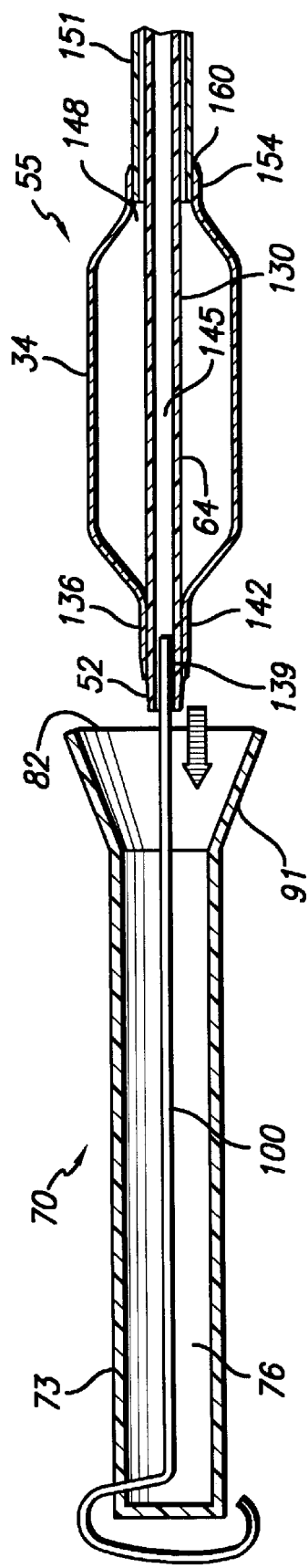
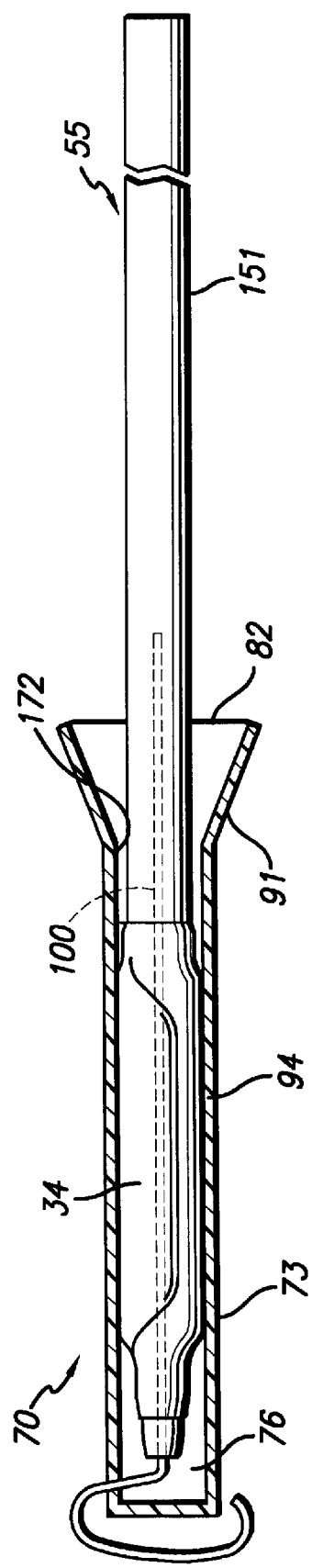
FIG. 6
FIG. 7

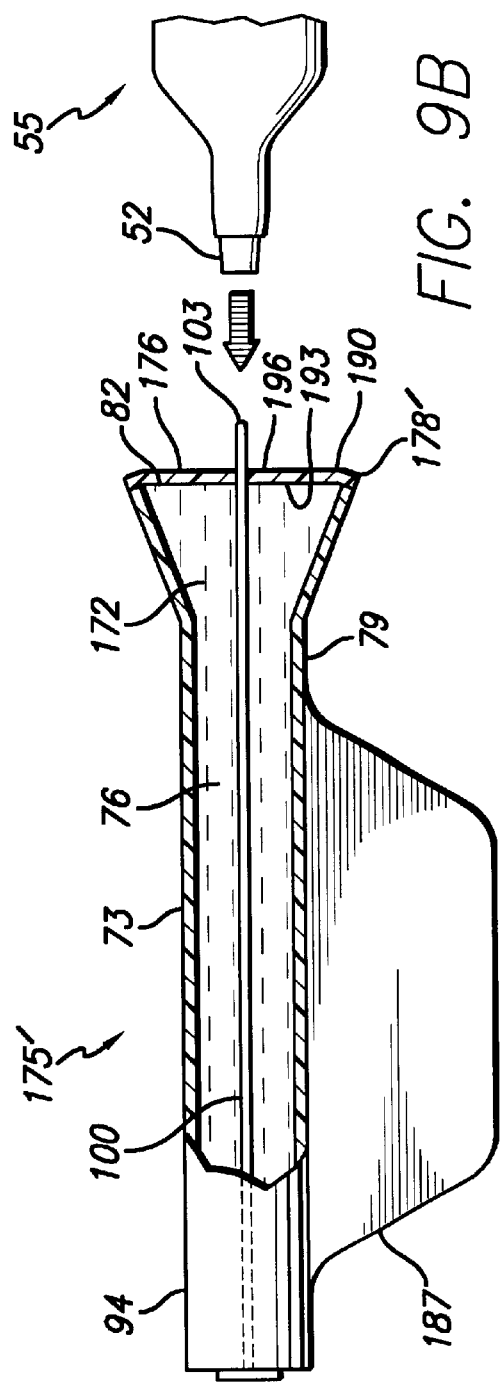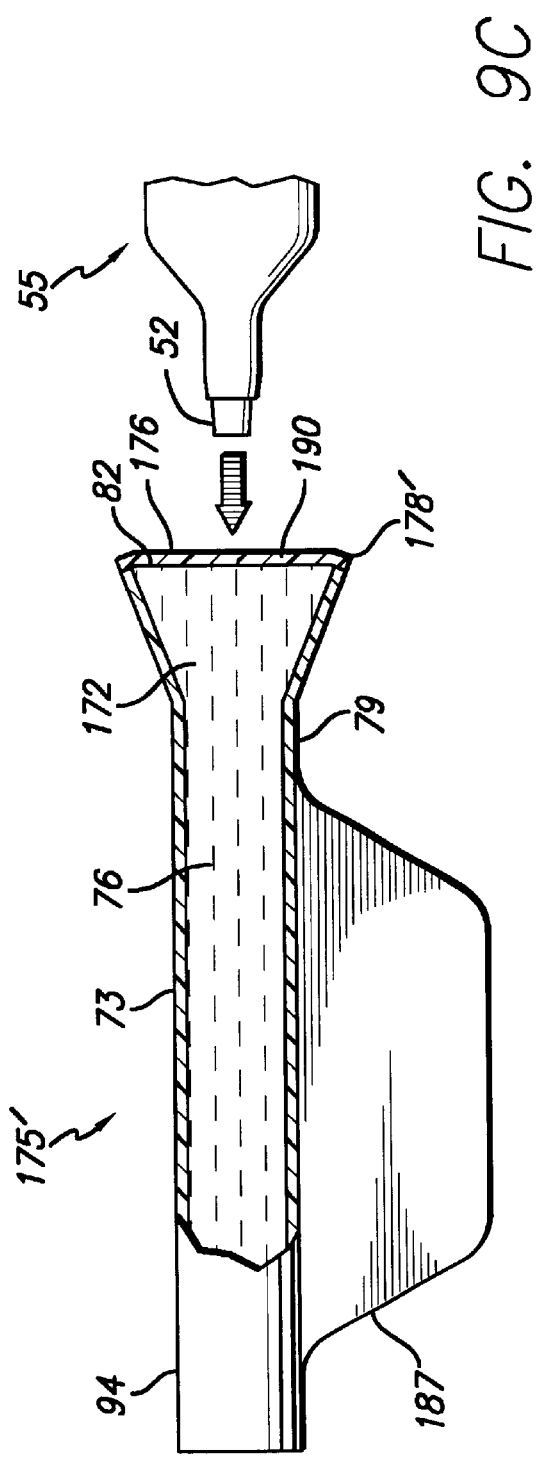

MEDICAL REGROOMING AND DRUG DELIVERY DEVICE

FIELD OF INVENTION

The invention relates to the field of intravascular delivery systems, therapeutic devices, imaging systems and more particularly to a regrooming device for balloon catheters.

BACKGROUND OF THE INVENTION

In percutaneous transluminal coronary angioplasty (PTCA) procedures, a guiding catheter is advanced until the distal tip of the guiding catheter is seated in the ostium of a desired coronary artery. A guide wire, positioned within an inner lumen of a dilatation catheter, is first advanced out of the distal end of the guiding catheter into the patient's coronary artery until the distal end of the guide wire crosses a lesion to be dilated. Then the dilatation catheter having an inflatable balloon on the distal portion thereof is advanced into the patient's coronary anatomy, over the previously introduced guide wire, until the balloon of the dilatation catheter is properly positioned across the lesion. Once properly positioned, the dilatation balloon is inflated with liquid one or more times to a predetermined size at relatively high pressures (e.g. greater than 8 atmospheres) so that the stenosis is compressed against the arterial wall and the wall expanded to open up the passageway. Generally, the inflated diameter of the balloon is approximately the same diameter as the native diameter of the body lumen being dilated so as to complete the dilatation but not overexpand the artery wall. After the balloon is finally deflated, blood flow resumes through the dilated artery and the dilatation catheter can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate and to strengthen the dilated area, physicians frequently implant an intravascular prosthesis, generally called a stent, inside the artery at the site of the lesion. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to a balloon angioplasty catheter, and expanded to a larger diameter by expansion of the balloon. The balloon is deflated to remove the catheter and the stent left in place within the artery at the site of the dilated lesion.

In the design of catheter balloons, balloon characteristics such as strength, flexibility and compliance must be tailored to provide optimal performance for a particular application. An important consideration is the outer diameter of the balloon in its deflated condition. This outer diameter affects the ease and ability of the dilatation catheter to pass through the guide catheter and through the coronary arteries leading to the stenosis, and thus is one of the critical factors to the successful performance of the device and treatment of the lesion.

In order to reduce the outer diameter of the balloon catheter in its uninflated (i.e. deflated) condition, it is common to fold and/or wrap the wings of the uninflated (i.e. deflated) balloon about the inner tubular member. When inflation fluid is applied to the deflated balloon, it causes the balloon wings to unwrap so that the balloon can expand to its full inflated state.

At times, it becomes necessary to regroom the balloon prior to actual use (e.g., introduction into the patient's body), as for example, after removal of the balloon catheter from its packaging and preparing it. In such an event, it is necessary to reshape the balloon.

The regrooming of the deflated balloon has been achieved by, thus far, for example, the physician or operator in the lab rewrapping the balloon around the tubular inner member by hand; the physician or operator loading the balloon onto the back end of the guidewire currently seated in the patient and using it as support for a regrooming sheath to be slidably fitted over the balloon in an attempt to refold the balloon which may introduce potential risk of damage to the patient's arteries; the physician or operator using a spare mandrel and a regrooming sheath and fitting the two together for rewrapping the balloon; and refolding the balloon by only using a regrooming sheath without a mandrel which often times causes kinking of the balloon thus making it non-functional or decreasing its performance.

Therefore, what has been needed is a more robust regrooming device suitable for use with balloon catheters and stent delivery systems. The present invention satisfies these and other needs.

SUMMARY OF THE INVENTION

The invention is directed to a regrooming device for use with balloon catheters and stent delivery systems, particularly catheter balloons which form wings when deflated. The regrooming device of the present invention comprises a tubular member having a proximal section and a distal section and an inner lumen 31 extending therein configured to slidably receive the deflated balloon so as to refold the deflated balloon. The regrooming device, furthermore, includes a mandrel disposed within the inner lumen of the regrooming device to guide the deflated balloon into the inner lumen so as to be centrally disposed within the lumen. The mandrel has a proximal end and a distal end which is secured to the distal section of the tubular member. The proximal end of the mandrel, preferably, protrudes out of the proximal section of the regrooming device.

The tubular member, preferably has a flared proximal end at its proximal section. The mandrel, preferably, has a curve or bend at its distal end. The curve is secured to the distal section of the tubular member by way of protruding out of an aperture at the distal section of the tubular member, with the curve butting up against the outer perimeter of the distal section of the tubular member.

Alternatively, the mandrel may not have a curve or bend in the distal section, but could be straight and secured to the tubular member with adhesive, a mechanical fastening device or crimping method.

Alternatively, the tubular member forming the regrooming device has an inner lumen defined, at least in part by a cylindrical member. The cylindrical member, may optionally, have a biocompatible fluid in or on its inner surface defining the lumen. The fluid may be either or both a lubricious fluid for facilitating entry and withdrawal of a balloon and a drug to be coated onto the balloon for delivery into the patient.

Alternatively, the regrooming device has a cap at the proximal section of the tubular member. The cap, preferably, has a notch therein for receiving the proximal end of the mandrel. The inner lumen of the tubular member is, at least partially, filled with fluid. The cap provides a liquid-tight seal with the proximal section of the tubular member, containing the fluid within the tubular member. The cap may be removed prior to the insertion of the balloon into the lumen of the regrooming device so that the balloon is coated with the fluid during the regrooming process.

Alternatively, the cap includes a membrane for holding the fluid in place within the inner lumen of the device. The membrane cap may receive a portion of the mandrel therein.

Alternatively, the device may be used for applying or reapplying a coating to a balloon or alternative technology device such as a balloon catheter for stent delivery or an ultrasonic catheter.

BRIEF DESCRIPTION OF THE DRAWINGS

FIG. 1 is a side elevational, partially cut away, view of a regrooming device embodying features of the invention.

FIG. 2 is a transverse sectional view of the regrooming device of FIG. 1 taken along line 2—2.

FIG. 3 is a side elevational, expanded, partially cut away, view of a portion of the interior surface of an alternative embodiment of the regrooming device of FIG. 1 having a spiral pattern thereon.

FIG. 4 is a side elevational, partially cut away, view of an alternative regrooming device embodying additional features of the invention.

FIG. 5 is a transverse sectional view of the regrooming device of FIG. 4 taken along line 5—5.

FIG. 6 is a side elevational, cut away, view of the regrooming device of FIG. 4 in operation with a balloon catheter being introduced into the inner lumen of the regrooming device.

FIG. 7 is a side elevational, partially cut away, view of the regrooming device of FIG. 6 with the balloon catheter (shown in parts) partially disposed within the regrooming device with the balloon folding.

FIG. 9(B) is a side elevational, partially cut away, view of an alternative embodiment of the regrooming device of FIG. 9(A) with the proximal end of the mandrel protruding outside the interior surface of the membrane.

FIG. 9(C) is a side elevational, partially cut away, view of an alternative embodiment of the regrooming device of FIG. 9(A) without a mandrel.

DETAILED DESCRIPTION OF THE INVENTION

Figure 8:
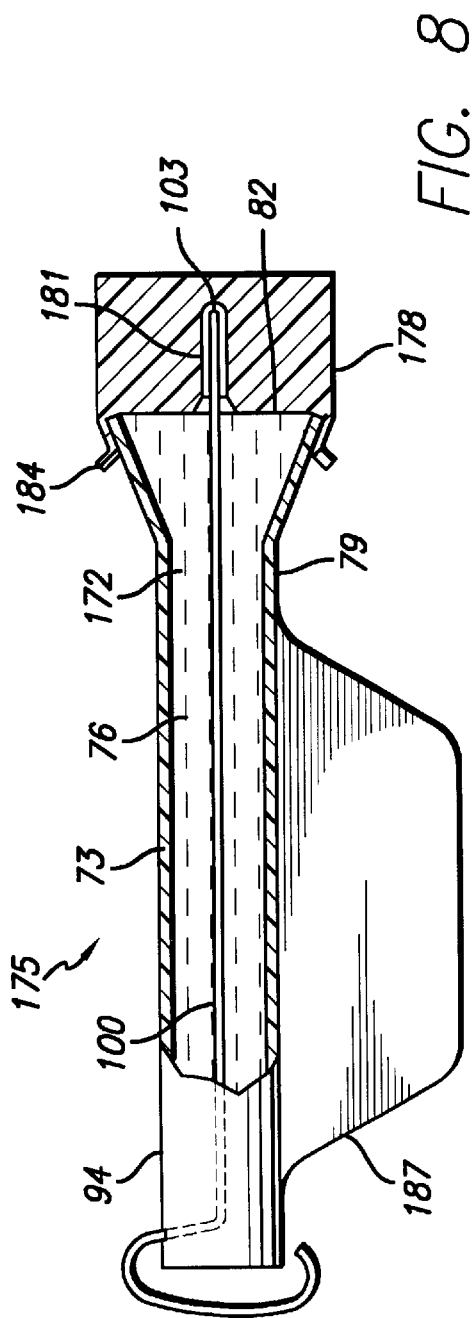
FIG. 8 is a side elevational, partially cut away, view of an alternative regrooming device embodying additional features of the invention and having a handle and a sealed interior to hold a fluid within the inner lumen of the regrooming device for coating the fluid onto the balloon during the regrooming process.

As used herein, the term balloon relates to any intracorporeal catheter having a balloon on a distal extremity, as in, but not limited to, angioplasty balloons, stent delivery systems, and drug delivery systems.

FIGS. 1 and 2 illustrate features of a regrooming device 10 embodying the present invention. The regrooming device 10 generally comprises an elongated tubular member 13, a proximal section 19 with a corresponding proximal aperture 22, a distal section 25 with a corresponding distal surface 28 and an inner lumen 31 extending along the length of the tubular member 13. The tubular member 13 is generally formed of Teflon, but other material such as nylon, polyethylene, polyethylene terathalate, Hytrel®, polyimide, polyamide or any mixture thereof may be used. The tubular member 13 is generally of sufficient length to allow for proper housing of a balloon 34 (FIG. 5) to effectively refold the wings (not shown) of the balloon 34 during the regrooming operation. Preferably, the tubular member 13 houses the entire length of the balloon 34. In particular, the tubular member 13 has a length in a range from about 5 to about 50 centimeters (cm), preferably from about 15 to about 45 cm. The inner lumen 31 is formed, at least in part, by a cylindrical member 37 which can be formed integral with the tubular member 13. The inner lumen 31 is configured to receive the balloon 34 and affect refolding thereof. Typically, the inner lumen 31 has a diameter of sufficient dimension to facilitate entry and withdrawal of the balloon 34 during the regrooming process. In particular, the inner lumen 31 has a diameter in a range from about 0.0001 to about 0.100 inch, and preferably, from about 0.001 to about 0.005 inch larger than the outer diameter of the balloon or stent delivery system. The inner surface of the tubular member 13 (or the inner surface of the cylindrical member 37) is preferably formed of or is coated with a lubricious material and has a smooth surface lining. Alternatively, a groove, ridge, or pattern may also be present to facilitate entry of the catheter into the regrooming device. In yet another embodiment, a specific pattern, for example a spiral pattern, may be incorporated onto the interior surface to facilitate the refolding of the balloon onto itself, as illustrated in FIG. 3.

A mandrel 40 having a proximal end 43 and a distal end 46 is disposed, preferably coaxially, within the inner lumen 31 of the tubular member 13. The proximal end 43 of the mandrel 40, preferably, protrudes out of the proximal section 19 of the tubular member 13 through aperture 22 by a length 49 sufficient to facilitate mounting a distal end 52 of a balloon catheter 55 and sliding the balloon catheter 55 over the mandrel 40 into the inner lumen 31. The protruding length 49 may range from zero (i.e. being flush with the aperture 22) to about 50 cm, preferably, from about 3 to about 5 cm. The mandrel 40 is secured at its distal end 46 to the distal section 25 of the tubular member 13. In FIG. 1, the mandrel 40 is secured at its distal end 46 to the distal surface 28 of the tubular member 13 through an aperture 58 at a joint 61. Alternatively, the joint 61 may be fixed by way of any one of means such as but not limited to, welding, adhesive, butt joints, and fasteners. The mandrel 40 may be formed of any suitable material of sufficient strength to guide the balloon catheter 55 into the inner lumen 31 of the regrooming device 10. Typically, the mandrel 40 is formed of stainless steel but can also be formed of other suitable material such as nitinol, platinum, titanium, tungsten rhenium or a mixture thereof. The mandrel 40 has a diameter sufficiently small to slidably receive a tubular member 64 (FIG. 6) of the balloon catheter 55 (FIG. 6), yet large enough to minimize unwanted slack as the tubular member 64 is moved along the length of the mandrel 40 (FIGS. 5 and 6). More particularly, the mandrel 40 has an outer diameter in a range from about 0.008 to about 0.050 inch, preferably, from about 0.016 to about 0.0175 inch for use with a typical 0.014 inch catheter system.

FIGS. 4 and 5 illustrate an embodiment of the features of the regrooming device of FIG. 1. A regrooming device 70 generally comprises an elongated tubular member 73, an inner lumen 76 extending along, all or part of, the length of the tubular member 73, and a proximal section 79 with a corresponding proximal aperture 82 and a distal section 85 with a corresponding distal surface 88, the proximal section 79 preferably having a flared proximal end 91 for easier insertion (regrooming) of the balloon 34. The inner lumen 76 is formed, at least in part, by a cylindrical member 94 which can be formed integral with the tubular member 73.

A mandrel 100 having a proximal end 103 and a distal end 106 with a bend or curve 109 is disposed, preferably coaxially, within the inner lumen 76. The proximal end 103 of the mandrel 100, preferably, protrudes out of the proximal section 79 of the tubular member 73 through a proximal aperture 82 by a length 115. The mandrel 100 is secured at its distal end 106 to the distal section 85 of the tubular member 73 by way of the curve 109 protruding out of a distal aperture 118 at the distal section 85 of the tubular member 73. The curve 109 butts up against the exterior of the tubular member 73 at the distal section 85.

By way of operation, the proximal end 103 of the mandrel 100 is inserted into the distal aperture 118 at the distal section 85 of the tubular member 73 and is then advanced through the length of the tubular member 73 toward its proximal section 79 until the curve 109 butts up against the exterior of the tubular member 73 at its distal section 85 thus securing the mandrel 100 in place. Alternatively, the curve 109 may be formed at the distal end 106 of the mandrel 100 after the proximal end 103 of the mandrel 100 has been advanced through the tubular member 73 toward its proximal section 79.

FIG. 6 illustrates features of the regrooming device of FIG. 4 in cooperation with the balloon catheter 55. Balloon 34 is mounted on a distal end 130 of the flexible tubular member 64 of the balloon catheter 55. The flexible tubular member 64 of the balloon catheter 55 may be formed of suitable material such as polymers, polymer blends or composite shafts commonly used in the art and known to practitioners skilled in the art. A distal end 136 of the balloon 34 is bonded to a distal extremity 139 of the flexible tubular member 64 to form an air-tight and liquid-tight distal seal 142 with respect to the same. The balloon 34 is coaxial with the tubular member 64 of the balloon catheter 55 as shown in FIG. 6. The flexible tubular member 64 of the balloon catheter 55 is provided with a guide wire lumen 145 through which a guide wire (not shown) may be extended. Means is provided for forming a balloon inflation lumen 148 substantially concentric with the flexible tubular member 64 and extending toward the distal end 130 of the flexible tubular member 64. The balloon inflation lumen 148 is formed, at least in part, by a flexible outer tubular member 151 which may be formed integral with the balloon 34. As can be further noted from FIG. 5, balloon 34 at its proximal end 154 is bonded to a distal extremity 157 of the outer tubular member 151 to form an air-tight and liquid-tight proximal seal 160 with respect to the same. In FIG. 6 the proximal end 103 of the mandrel 100 is illustrated as disposed, preferably coaxially, within the guide wire lumen 145 of the tubular member 64.

In operation, the regrooming device 70 is held by an operator at some portion while the distal end 130 of the tubular member 64 is placed over the proximal end 103 of the mandrel 100 (FIGS. 6 and 7). The balloon catheter 55 is slidably advanced toward the distal section 85 of the tubular member 73 to effectuate the refolding of the balloon 34. The balloon 34 is then retracted toward the proximal section 79 of the tubular member 73. The balloon catheter 55 is then removed from the mandrel 100 yielding a refolded balloon.

In an embodiment, features of which are illustrated in FIG. 7, and wherein like references refer to like parts, cylindrical member 94 of inner lumen 76 is coated with a suitable biocompatible fluid or coating 172. The fluid 172 may be either or both a lubricious material for enhancing the slidability of the balloon 34 through the intracorporeal and a drug to be delivered on the exterior of the same. Examples of the fluid 172 include, but are not limited to, PEO (polyethylene oxide) or sterile saline. As the balloon 34 is advanced or retracted through the tubular member 73, the fluid 172 is coated onto the balloon 34.

In one embodiment, features of which are illustrated in FIG. 8 and wherein like references refer to like parts, the proximal section 79 of the tubular member 73 of a regrooming device 175 is provided with a cap 178 for providing a liquid-tight seal with the proximal aperture 82 and providing a sealed interior to hold the fluid 172 within the inner lumen 76 of the regrooming device 175. In the embodiment featured in FIG. 7, the cap 178, preferably, has a notch 181 therein for receiving the proximal end 103 of the mandrel 100 and, preferably, has a pair of flanges 184 for securely holding in place the cap 178 on the proximal section 79 of the tubular member 73. Alternatively, the cap 178 may be threaded allowing it to be screwed onto the aperture proximal 82.

The fluid 172, for coating onto the balloon 34 during the regrooming process, may then be contained in the inner lumen 76 of the capped regrooming device 175. The regrooming device 175 can further be provided with a handle 187, extending along, at least a portion of, the length of the tubular member 73 for ease of handling by the operator. During operation, the cap 178 is removed before the balloon catheter 55 is inserted into the inner lumen 76.

Figure 9A:
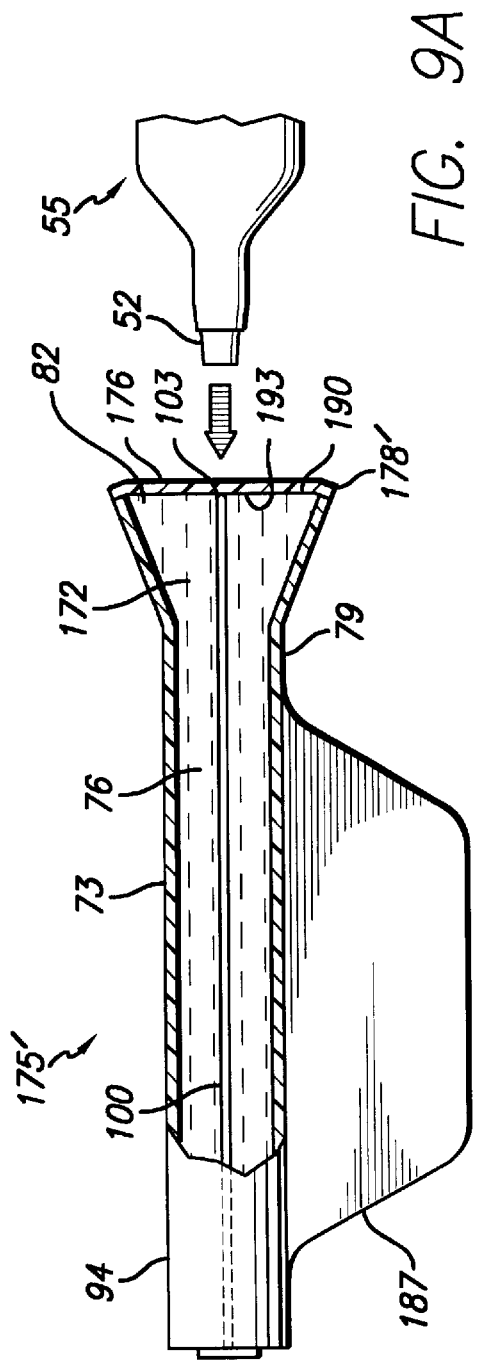
FIG. 9(A) is a side elevational, partially cut away, view of an alternative embodiment of the regrooming device of FIG. 8 having a membrane attached at the proximal aperture of the device for sealing the fluid therein, with the proximal end of the mandrel resting within the interior surface of the membrane.

Now referring to FIG. 9(A), a cap 178' is sealingly attached onto the proximal aperture 82, of a device 175', the cap 178' being in the form of, or include, a membrane 190. The membrane 190 may be formed of elastomeric material allowing the catheter end 52 to be inserted into the inner lumen 76 of the device for regrooming, and thereafter being retracted out with the membrane 190 holding the fluid 172 in place within inner lumen 76. The proximal end 103 of the mandrel 100 may be securely attached to the interior surface 193 of the member 190, or alternatively as shown in FIG. 9(B), may protrude out of the exterior surface 196 of the membrane 190, either way, allowing the distal end 52 of the balloon catheter 55 to be slidably advanced over the mandrel 100 toward the distal end of the device 175' through the inner lumen 76. The balloon catheter 55 is thereafter retraced out of the device 175', as described above, with the membrane 190 sealing, at least in part, upon itself, to maintain the fluid 172 therein.

Alternatively, the device 175' may not include a mandrel 100, as shown in FIG. 9(C), in which case, the distal end 52 of the balloon catheter 55 is inserted through the exterior surface of the membrane 190 into the inner lumen 76.

In yet another embodiment, the cylindrical member 94 may include a permeable material (not shown), such as a sponge, for releasably containing the desirable fluid 172. As the balloon 34 is moved through inner lumen 76, fluid 172 is coated thereon from the permeable material, thereby coating the balloon 34 with the fluid 172.

It should be appreciated that although in describing the invention, a device for regrooming a balloon on a balloon catheter has been described, the same may be used for applying a coating such as a lubricant or drug onto a balloon, or an alternative technology device such as a balloon catheter for stent delivery or an ultrasonic catheter. For example, the same may be used for applying a lubricant onto a stent or an atherectomy product.

It will be apparent from the foregoing that, while particular forms of the invention have been illustrated and described, various modifications can be made without departing from the spirit and scope of the invention. Although individual features of embodiments of the invention may be described or shown in some of the drawings and not in others, those skilled in the art will recognize that individual features of one embodiment of the invention can be combined with any or all the features of another embodiment. Other modifications may be made without departing from the scope of the invention.

What is claimed is:

1. A regrooming device for a balloon catheter, comprising:
    a tubular member having a proximal section, a distal section, and an inner lumen extending therein configured to receive a balloon of a balloon catheter; and
    a mandrel disposed within the inner lumen and having a proximal end configured to enter a guide wire lumen at a distal section of the balloon catheter to facilitate guiding the distal section of the catheter into the inner lumen of the regrooming device, and a distal end secured to the distal section of the tubular member.

2. The device of claim 1 wherein the tubular member has a length sufficient to allow for proper housing of the balloon of the balloon catheter to effectively refold the wings of the balloon during regrooming operation.

3. The device of claim 2 wherein the tubular member has a length in a range from about 5 to about 50 cm.

4. The device of claim 3 wherein the tubular member has a length in a range from about 15 to about 45 cm.

5. The device of claim 1 wherein the inner lumen has a diameter of sufficient dimension to facilitate entry and withdrawal of the balloon during the regrooming process.

6. The device of claim 5 wherein the inner lumen has a diameter in a range from about 0.008 to about 0.050 inch.

7. The device of claim 6 wherein the inner lumen has a diameter in a range from about 0.016 to about 0.0175 inch.

8. The device of claim 1 wherein the proximal end of the mandrel protrudes out of the proximal section of the tubular member by a length sufficient to facilitate moving the distal end of the catheter and sliding the catheter over the mandrel into the inner lumen.

9. The device of claim 8 wherein the length of the mandrel protruding out of the proximal section of the tubular member is in a range from about 0.0 to about 50 mm.

10. The device of claim 9 wherein the length of the mandrel protruding out of the proximal section of the tubular member is in a range from about 3 to about 5 mm.

11. The device of claim 1 wherein the mandrel is disposed coaxially within the inner lumen of the regrooming device.

12. The device of claim 1 wherein
    the tubular member further includes
        an aperture at the distal section of the tubular member, and wherein the distal end of the mandrel has a curve secured at the distal section of the tubular member and protruding out of the aperture with the curve butting up against the outer perimeter of the tubular member.

13. The device of claim 1 wherein the proximal section has a flared proximal end.

14. A regrooming device for a balloon catheter, comprising:
    a tubular member having a proximal section, a distal section, and an inner lumen extending therein configured to receive a balloon of a balloon catheter, the lumen defined at least in part by a cylindrical member having a biocompatible fluid thereon; and
    a mandrel disposed within the inner lumen and having a proximal end configured to enter a guide wire lumen at a distal section of the balloon catheter to facilitate guiding the distal section of the catheter into the inner lumen of the regrooming device, and a distal end secured to the distal section of the tubular member.

15. A regrooming device for a balloon catheter, comprising:
    a tubular member having a proximal section, a distal section, and an inner lumen extending therein configured to receive a balloon of a balloon catheter;
    a mandrel disposed within the inner lumen and having a proximal end configured to enter a guide wire lumen at a distal section of the balloon catheter to facilitate guiding the distal section of the catheter into the inner lumen of the regrooming device, and a distal end secured to the distal section of the tubular member; and
    a cap at the proximal section of the tubular member for providing a sealed interior to hold a fluid within the inner lumen of the regrooming device.

16. The device of claim 15 wherein the cap has a notch therein for receiving, at least in part, the proximal end of the mandrel.

17. The device of claim 15 wherein the cap includes a membrane.

18. The device of claim 17 wherein the cap receives at least a portion of the proximal end of the mandrel therein.

19. The device of claim 15 further including a biocompatible fluid.

20. The device of claim 19 wherein the biocompatible fluid comprises a fluid selected from the group consisting of polyethylene oxides and saline.

* * * * *